(12) United States Patent
Yamamoto et al.

(10) Patent No.: US 7,651,993 B2
(45) Date of Patent: Jan. 26, 2010

(54) FLUORINE-CONTAINING POLYMER AND SOIL RELEASE AGENT

(75) Inventors: Ikuo Yamamoto, Osaka (JP); Norimasa Uesugi, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 12/026,243

(22) Filed: Feb. 5, 2008

(65) Prior Publication Data

US 2008/0194450 A1 Aug. 14, 2008

(30) Foreign Application Priority Data

Feb. 6, 2007 (JP) .............................. 2007-026365

(51) Int. Cl.
*C11D 3/00* (2006.01)
(52) U.S. Cl. .......................... 510/299; 106/2; 252/8.61; 252/8.62; 427/385.5; 427/379; 526/243; 560/222
(58) Field of Classification Search ................ 8/115.51; 510/299; 526/243; 560/222; 427/385.5, 427/379; 252/8.61, 8.62; 106/2
See application file for complete search history.

(56) References Cited

U.S. PATENT DOCUMENTS

| 4,695,488 A | 9/1987 | Hisamoto et al. |
| 6,274,060 B1 | 8/2001 | Sakashita et al. |

FOREIGN PATENT DOCUMENTS

| EP | 0195323 A2 | 9/1986 |
| JP | 53-134786 | 11/1978 |
| JP | 59-204980 | 11/1984 |
| JP | 63-75082 A | * 10/1986 |
| JP | 62-7782 | 1/1987 |
| JP | 2000-290640 | 10/2000 |
| WO | WO 2007/007743 A1 | * 1/2007 |

OTHER PUBLICATIONS

Patsy O. Sherman, et al.; "Textile Characteristics Affecting the Release of Soil During Laundering: Part II: Fluorochemical Soil-Release Textile Finishes"; Textile Research Journal; May 1969; pp. 449-459.
"Preliminary Risk Assessment of the Developmental Toxicity Associated with Exposure to Perfluorooctanoic Acid and Its Salts"; U.S. Environmental Protection Agency. Office of Pollution Prevention and Toxics Risk Assessment Division; Apr. 10, 2003.
OPPT Fact Sheet; EPA; Apr. 14, 2003.
"EPA Intensifies Scientific Investigation of a Chemical Processing Aid"; Environmental News; EPA; Monday, Apr. 14, 2003.
"Perfluorooctanoic Acid (PFOA), Fluorinated Telomers; Request for Comment, Solicitation of Interested Parties for Enforceable Consent Agreement Development, and Notice of Public Meeting"; Environmental Protection Agency; Federal Register; vol. 68, No. 73; Wednesday, Apr. 16, 2003/Notices; pp. 18626-18633.

* cited by examiner

Primary Examiner—Harold Pyon
Assistant Examiner—Bijan Ahvazi
(74) Attorney, Agent, or Firm—Sughrue Mion, PLLC

(57) ABSTRACT

A fluorine-containing copolymer including: (A) repeating units derived from a fluorine-containing macromonomer of the general formula: $CH_2=C(-X)-COO-(Y)_1-Z-M^f_m M^r_n-H$ (I) wherein X, Y, Z and $M^f_m M^r_n$ are as described herein, and (B) repeating units derived from a polyalkyleneglycol (meth)acrylate.

10 Claims, 1 Drawing Sheet

FLUORINE-CONTAINING POLYMER AND SOIL RELEASE AGENT

BACKGROUND OF THE INVENTION

1. Field of the Invention

The present invention relates to a fluorine-containing copolymer which imparts excellent oil repellency, stain-proofing properties and soil releasability to articles to be treated such as textiles, and is excellent in washing-durability.

2. Background Art

As a stain-proofing agent which imparts water- and oil-repellency to fiber woven fabrics and the like, and also enables easy removal of stains adhered on fibers through washing, a copolymer of a (meth)acrylate ester having a fluoroalkyl group (hereinafter also referred to as a fluorine-containing compound) and a hydrophilic group-containing compound is known (see JP-A-53-134786, JP-A-59-204900 and JP-A-62-7782).

However, fiber woven fabrics and the like treated with these fluorine-containing copolymers do not always have satisfactory washing durability and also have a tendency not to have sufficient and satisfactory soil releasability against persistent soils (for example, waste oil such as used engine oil).

It is considered that oil repellency and flip-flop properties are important so as to obtain sufficient soil releasability and, in air, perfluoroalkyl groups (hereinafter abbreviated to Rf groups) are oriented on the surface and high oil repellency is exhibited. In contrast, in water, Rf groups retract and hydrophilic groups are oriented on the surface, and thus soils are easily removed. Flip-flop properties are properties in which a surface molecular structure varies depending on the environment in air and water, and are proposed by Sherman et al. [P. Sherman, S. Smith, B, Johannessen, Textile Research Journal, 39, 499 (1969)]

When the Rf group has a short chain length, oil repellency tends to deteriorate as crystallinity of Rf decreases and an article to be treated is easily contaminated with oil soils. Therefore, a stain-proofing agent having Rf group containing substantially 6 or more carbon atoms has been used (see JP-A-53-134786 and JP-A-2000-290640).

Further, recently, with respect to a compound containing the Rf group having 8 carbon atoms obtained by telomerization, Federal Register (FR Vol. 68, No. 73/Apr. 16, 2003 [FRL-2303-8]; EPA Environmental News FOR RELEASE: MONDAY APR. 14, 2003 EPA INTENSIFIES SCIENTIFIC INVESTIGATION OF A CHEMICAL PROCESSING AID; and EPA OPPT FACT SHEET Apr. 14, 2003 have announced that a "telomer" may possibly metabolize or decompose to perfluorooctanoic acid (hereinafter referred to as "PFOA").

EPA (Environmental Protection Agency of USA) has announced that the EPA intensifies the scientific investigation on PFOA (cf. EPA Report "PRELIMINARY RISK ASSESSMENT OF THE DEVELOPMENTAL TOXICITY ASSOCIATED WITH EXPOSURE TO PERFLUOROOCTANOIC ACID AND ITS SALTS").

DISCLOSURE OF THE INVENTION

Problems to be Solved by the Invention

An object of the present invention is to provide a soil release agent which imparts excellent oil repellency, stain-proofing properties and soil releasability to fiber woven fabrics and the like while maintaining washing durability, and also provides a soil release agent which is similarly excellent even if the number of carbon atoms of an Rf group is decreased to less than 8, which is shorter than that in the prior art.

The present invention provides a fluorine-containing copolymer comprising:

(A) repeating units derived from a fluorine-containing macromonomer of the general formula:

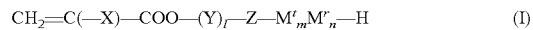

$$CH_2=C(-X)-COO-(Y)_l-Z-M^f_mM^r_n-H \quad (I)$$

wherein X is a hydrogen atom or a methyl group;
Y is $-CH_2CH(OH)CH_2-$ or $R^1-NHCO-$ ($R^1$ is $-(CH_2CH_2O)_a(CH_2)_b-$, a is 0 to 20, and b is 1 to 20);
l is 0 or 1;
Z is $-L_1-L_2-S-$ ($L_1$ is a direct bond, $-O-$, $COO-$ or $NH-$, $L_2$ is an alkylene group having 1 to 20 carbon atoms or an aryl group having 6 to 20 carbon atoms, and S is a sulfur atom);
$M^f_mM^r_n$ is a fluorochemical oligomer having m repeating units derived from a fluorine-containing monomer ($M^f$) and n repeating units derived from a fluorine-free monomer ($M^r$) (m is 2 to 50 and n is 0 to 20), and (B) repeating units derived from a polyalkyleneglycol (meth)acrylate.

The fluorine-containing copolymer of the present invention functions as an active component of a soil release agent.

The present invention also provides a fluorine-containing compound (that is, a fluorine-containing macromer) of the general formula:

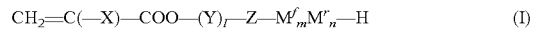

$$CH_2=C(-X)-COO-(Y)_l-Z-M^f_mM^r_n-H \quad (I)$$

wherein X is a hydrogen atom or a methyl group;
Y is $-CH_2CH(OH)CH_2-$ or $R^1-NHCO-$ ($R^1$ is $-(CH_2CH_2O)_a(CH_2)_b-$, a is 0 to 20, and b is 1 to 20);
l is 0 or 1;
Z is $-L_1-L_2-S-$ ($L_1$ is a direct bond, $-O-$, $COO-$ or $NH-$, $L_2$ is an alkylene group having 1 to 20 carbon atoms or an aryl group having 6 to 20 carbon atoms, and S is a sulfur atom);
$M^f_mM^r_n$ is a fluorochemical oligomer having m repeating units derived from a fluorine-containing monomer ($M^f$) and n repeating units derived from a fluorine-free monomer ($M^r$) (m is 2 to 50 and n is 0 to 20).

EFFECT OF THE INVENTION

According to the present invention, a fluorine-containing copolymer constituting a soil release agent, which imparts excellent oil repellency, stain-proofing properties and soil releasability to textiles and is also excellent in washing durability, is obtained.

Also, a similarly excellent above-mentioned soil release agent is obtained, even if the number of carbon atoms of a perfluoroalkyl group in the fluorine-containing copolymer is less than 8.

In the prior art, when the Rf group has less than 8 carbon atoms, soil releasability deteriorates. According to the present invention, by using a polymerizable monomer having an Rf group of less than 8 carbon atoms, preparing a macromonomer and polymerizing the macromonomer with a hydrophilic component, the fluorine component can be localized. Therefore, the fluorine component can act efficiently and both of high flip-flop properties and oil repellency in air are maintained and excellent soil releasability is obtained in comparison with the prior art soil release agents, even if a fluorine content in the copolymer is low.

MODE FOR CARRYING OUT THE INVENTION

Figure 1:
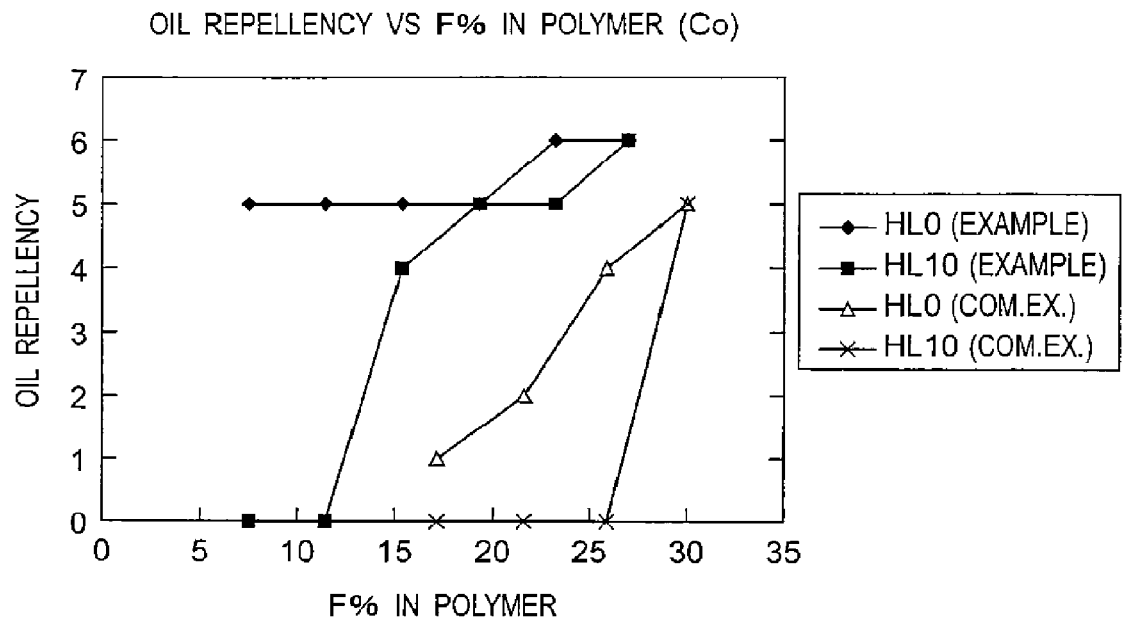
FIG. 1 is a graph showing the relationship between a fluorine content in a polymer (% by weight) and oil repellency.

The fluorine-containing copolymer of the present invention is a fluorine-containing copolymer comprising (A) the repeating unit derived from the fluorine macromonomer (a) and (B) the repeating unit derived from the polyalkyleneglycol (meth)acrylate (b) as essential components.

If necessary, the fluorine-containing copolymer may have (C) a repeating unit derived from a monomer other than the monomers (a) and (b), which has an unsaturated double bond capable of copolymerizing with the monomers (a) and (b).

In the present invention, the repeating unit (A) is composed of a fluorine-containing macromonomer (a) of formula (I).

In the formula (I), specific examples of Y include —$CH_2CH(OH)CH_2$— and —$(CH_2)_b NHCO$— (b is the number of 1 to 10).

Specific examples of Z include —$O(CH)_d$—S—, (d is the number of 1 to 10).

The fluorine-containing macromonomer (a) can be synthesized as follows:

The fluorine-containing monomer ($M^f$) alone, or a mixture of the fluorine-containing monomer ($M^f$) and the fluorine-free monomer ($M^r$) is radically polymerized by the use of a radical initiator in the presence of an active hydrogen-containing mercaptan as a chain transfer agent to give a reactive fluorine-containing oligomer having active hydrogen. The reactive fluorine-containing oligomer is reacted with a (meth) acryloyl monomer having a functional group capable of reacting with active hydrogen to give the fluorine-containing macromonomer (a) of the formula (I).

Hereinafter, the present invention is explained in detail.

In the above-mentioned formula (I), the fluorine-containing monomer ($M^f$) is a fluorine-containing monomer having a polymerizable unsaturated double bond.

The fluorine-containing monomer ($M^f$) is preferably of the general formula:

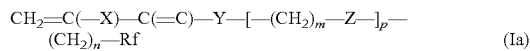

$$CH_2=C(-X)-C(=C)-Y-[-(CH_2)_m-Z-]_p-(CH_2)_n-Rf \quad (Ia)$$

wherein X is a hydrogen atom, a methyl group, a straight-chain or branched alkyl group having 1 to 21 carbon atoms, a fluorine atom, a chlorine atom, a bromine atom, a iodine atom, a $CFX^1X^2$ group (wherein $X^1$ and $X^2$ represent a hydrogen atom, a fluorine atom, a chlorine atom, a bromine atom, or a iodine atom), a cyano group, a straight-chain or branched fluoroalkyl group having 1 to 21 carbon atoms, a substituted or an unsubstituted benzyl group, or a substituted or an unsubstituted phenyl group;

Y is —O— or —NH—;

Z is —S— or —$SO_2$—;

Rf is a fluoroalkyl group having 1 to 21, particularly 1 to 6 carbon atoms;

m is 1 to 10, n is 0 to 10, and p is 0 or 1.

In the general formula (Ia), mentioned is the example wherein p and n is 0, and Y is a —$OCH_2CH_2N(R^2)SO_2$— group ($R^2$ is an alkyl group having 1 to 4 carbon atoms) or —$OCH_2CH(OCOCH_3)CH_2$— group.

Other preferable examples of the fluorine-containing monomer ($M^f$) include a fluoroolefin (having, for example, 3 to 20 carbon atoms) such as $CF_3(CF_2)_7CH=CH_2$, $C_8F_{17}$—$C_6H_4$—$CH_2O$—$COCH=CH_2$ and $C_5F_{11}$—$C_6H_4$—$CH_2O$—$COC(CH_3)=CH_2$.

The fluorine-containing monomer ($M^f$) has a perfluoroalkyl group and/or a partially fluorinated fluoroalkyl group. The perfluoroalkyl group is preferable. The carbon number of the Rf group is 1 to 21. The upper limit of the carbon number of the Rf group may be 8, for example, 6, particularly 5, especially 4. Examples of the Rf group include —$CF_3$, —$CF_2CF_3$, —$CF_2CF_2CF_3$, —$CF(CF_3)_2$, —$CF_2CF_2CF_2CF_3$, —$CF_2CF (CF_3)_2$, —$C(CF_3)_3$, —$(CF_2)_4CF_3$, —$(CF_2)_2CF (CF_3)_2$, —$CF_2C(CF_3)_3$, —$CF(CF_3)CF_2CF_2CF_3$, —$(CF_2)_5 CF_3$, —$(CF_2)_3CF(CF_3)_2$, —$(CF_2)_4CF(CF_3)_2$, —$(CF_2)_7CF_3$, —$(CF_2)_5CF(CF_3)_2$, —$(CF_2)_6CF(CF_3)_2$, and —$(CF_2)_9CF_3$ The fluorine-containing monomer ($M^f$) may be used alone or a combination of at least two.

Examples of the fluorine-containing monomer ($M^f$) include, for example, the followings:

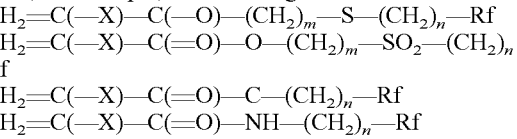

$CH_2=C(-X)-C(=O)-(CH_2)_m-S-(CH_2)_n-Rf$
$CH_2=C(-X)-C(=O)-O-(CH_2)_m-SO_2-(CH_2)_n-Rf$
$CH_2=C(-X)-C(=O)-C-(CH_2)_n-Rf$
$CH_2=C(-X)-C(=O)-NH-(CH_2)_n-Rf$ wherein X is a hydrogen atom, a methyl group, a fluorine atom, a chlorine atom, a bromine atom, a iodine atom, a $CFX^1X^2$ group (wherein $X^1$ and $X^2$ represent a hydrogen atom, a fluorine atom, or a chlorine atom), a cyano group, a straight-chain or branched fluoroalkyl group having 1 to 20 carbon atoms, a substituted or an unsubstituted benzyl group, or a substituted or an unsubstituted phenyl group;

Rf is a fluoroalkyl group having 1 to 21, particularly 1 to 6 carbon atoms;

m is 1 to 10, n is 0 to 10.

Specific examples of the fluorine-containing monomer (a) include, but are not limited to, the following:

$CH_2=C(-H)-C(=O)-O-(CH_2)_2-S-Rf$
$CH_2=C(-H)-C(=O)-O-(CH_2)_2-S-(CH_2)_2-Rf$
$CH_2=C(-H)-C(=O)-O-(CH_2)_3-SO_2-Rf$
$CH_2=C(-H)-C(=O)-O-(CH_2)_2-SO_2-(CH_2)_2-Rf$
$CH_2=C(-H)-C(=O)-O-(CH_2)_2-Rf$
$CH_2=C(-H)-C(=O)-NH-(CH_2)_2-Rf$
$CH_2=C(-H)-C(=O)-OCH_2CH_2N(C_2H_5)SO_2-Rf$
$CH_2=C(-H)-C(=O)-OCH_2CH_2N(CH_3)SO_2-Rf$
$CH_2=C(-H)-C(=O)-OCH_2CH(OCOCH_3)CH_2-Rf$
$CH_2=C(-CH_3)-C(=O)-O-(CH_2)_2-S-Rf$
$CH_2=C(-CH_3)-C(=O)-O-(CH_2)_2-S-(CH_2)_2-Rf$
$CH_2=C(-CH_3)-C(=O)-O-(CH_2)_3-SO_2-Rf$
$CH_2=C(-CH_3)-C(=O)-O-(CH_2)_2-SO_2-(CH_2)_2-Rf$
$CH_2=C(-CH_3)-C(=O)-O-(CH_2)_2-Rf$
$CH_2=C(-CH_3)-C(=O)-NH-(CH_2)_2-Rf$
$CH_2=C(-CH_3)-C(=O)-OCH_2CH_2N(C_2H_5)SO_2-Rf$

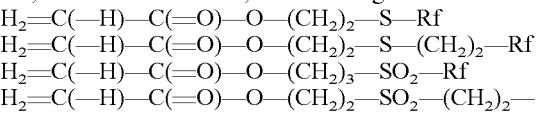

$CH_2=C(-C_1H_3)-C(=O)-OCH_2CH_2N(CH_3)SO_2-Rf$
$CH_2=C(-CH_3)-C(=O)-OCH_2CH(OCOCH_3)CH_2-Rf$
$CH_2=C(-F)-C(=O)-O-(CH_2)_2-S-Rf$

CH₂=C(—F)—C(=O)—O—(CH₂)₂—S—(CH₂)₂—Rf
CH₂=C(—F)—C(=O)—O—(CH₂)₂—SO₂—Rf
CH₂=C(—F)—C(=O)—O—(CH₂)₂—SO₂—(CH₂)₂—Rf
CH₂=C(—F)—C(=O)—O—(CH₂)₂—Rf
CH₂=C(—F)—C(=O)—NH—(CH₂)₂—Rf
CH₂=C(—Cl)—C(=O₂)—O—(CH₂)₂—S—Rf
CH₂=C(—Cl)—C(=O)—O—(CH₂)₂—S—(CH₂)₂—Rf
CH₂=C(—Cl)—C(=O)—O—(CH₂)₂—SO₂—Rf
CH₂=C(—Cl)—C(=O)—O—(CH₂)₂—SO₂—(CH₂)₂—Rf
CH₂=C(—Cl)—C(=O)—O—(CH₂)₂—Rf
CH₂=C(—Cl)—C(=O)—NH—(CH₂)₂—Rf
CH₂=C(—CF₃)—C(=O)—O—(CH₂)₂—S—Rf
CH₂=C(—CF₃)—C(=O)—O—(CH₂)₂—S—(CH₂)₂—Rf
CH₂=C(—CF₃)—C(=O)—O—(CH₂)₂—SO₂—Rf
CH₂=C(—CF₃)—C(=O₂)—O—(CH₂)₂—SO₂—(CH₂)₂—Rf
CH₂=C(—CF₃)—C(=O)—O—(CH₂)₂—Rf
CH₂=C(—CF₃)—C(=O)—NH—(CH₂)₂—Rf
CH₂=C(—CF₂H)—C(=O)—O—(CH₂)₂—S—Rf
CH₂=C(—CF₂H)—C(=O)—O—(CH₂)₂—S—(CH₂)₂—Rf
CH₂=C(—CF₂H)—C(=O)—O—(CH₂)₂—SO₂—Rf
CH₂=C(—CF₂H)—C(=O)—O—(CH₂)₂—SO₂—(CH₂)₂—Rf
CH₂=C(—CF₂H)—C(=O)—O—(CH₂)₂—Rf
CH₂=C(—CF₂H)—C(=O)—NH—(CH₂)₂—Rf
CH₂=C(—CN)—C(=O)—O—(CH₂)₂—S—Rf
CH₂=C(—CN)—C(=O)—O—(CH₂)₂—S—(CH₂)₂—Rf
CH₂=C(—CN)—C(=O)—O—(CH₂)₂—SO₂—Rf
CH₂=C(—CN)—C(=O)—O—(CH₂)₂—SO₂—(CH₂)₂—Rf
CH₂=C(—CN)—C(=O)—C—(CH₂)₂—Rf
CH₂=C(—CN)—C(=O)—NH—(CH₂)₂—Rf
CH₂=C(—CF₂CF₃)—C(=O)—O—(CH₂)₂—S—Rf
CH₂=C(—CF₂CF₃)—C(=O)—O—(CH₂)₂—S—(CH₂)₂—Rf
CH₂=C(—CF₂CF₃)—C(=O)—O—(CH₂)₂—SO₂—Rf
CH₂=C(—CF₂CF₃)—C(=O)—O—(CH₂)₂—SO₂—(CH₂)₂—Rf
CH₂=C(—CF₂CF₃)—C(=O)—O—(CH₂)₂—Rf
CH₂=C(—CF₂CF₃)—C(=O)—NH—(CH₂)₂—Rf
CH₂=C(—F)—C(=O)—O—(CH₂)₃—S—Rf
CH₂=C(—F)—C(=O)—O—(CH₂)₃—S—(CH₂)₂—Rf
CH₂=C(—F)—C(=O)—O—(CH₂)₃—SO₂—Rf
CH₂=C(—F)—C(=O)—O—(CH₂)₃—SO₂—(CH₂)₂—Rf
CH₂=C(—F)—C(=O)—O—(CH₂)₃—Rf
CH₂=C(—F)—C(=O)—NH—(CH₂)₃—Rf
CH₂=C(—Cl)—C(=O)—O—(CH₂)₃—S—Rf
CH₂=C(—Cl)—C(=O)—O—(CH₂)₃—S—(CH₂)₂—Rf
CH₂=C(—Cl)—C(=O)—O—(CH₂)₃—SO₂—Rf
CH₂=C(—Cl)—C(=O)—O—(CH₂)₃—SO₂—(CH₂)₂—Rf
CH₂=C(—CF₃)—C(=O)—C—(CH₂)₃—S—Rf
CH₂=C(—CF₃)—C(=O)—C—(CH₂)₃—S—(CH₂)₂—Rf
CH₂=C(—CF₃)—C(=O)—C—(CH₂)₃—SO₂—Rf
CH₂=C(—CF₃)—C(=O)—C—(CH₂)₃—SO₂—(CH₂)₂—Rf
CH₂=C(—CF₂H)—C(=O)—C—(CH₂)₃—S—Rf
CH₂=C(—CF₂H)—C(=O)—O—(CH₂)₃—S—(CH₂)₂—Rf
CH₂=C(—CF₂H)—C(=O)—C—(CH₂)₃—SO₂—Rf
CH₂=C(—CF₂H)—C(=O)—O—(CH₂)₃—SO₂—(CH₂)₂—Rf
CH₂=C(—CN)—C(=O)—O—(CH₂)₃—S—Rf
CH₂=C(—CN)—C(=O)—O—(CH₂)₃—S—(CH₂)₂—Rf
CH₂=C(—CN)—C(=O)—O—(CH₂)₃—SO₂—Rf
CH₂=C(—CN)—C(=O)—C—(CH₂)₃—SO₂—(CH₂)₂—Rf
CH₂=C(—CF₂CF₃)—C(=O)—C—(CH₂)₃—S—Rf
CH₂=C(—CF₂CF₃)—C(=O)—O—(CH₂)₃—S—(CH₂)₂—Rf
CH₂=C(—CF₂CF₃)—C(=O)—O—(CH₂)₃—SO₂—Rf
CH₂=C(—CF₂CF₃)—C(=O)—O—(CH₂)₂—SO₂—(CH₂)₂—Rf

Rf is a fluoroalkyl group having 1 to 21, particularly 1 to 6 carbon atoms.

Specific examples of oligomer ($M^f_m$) derived from the fluorine-containing monomer ($M^f$) are as follows:

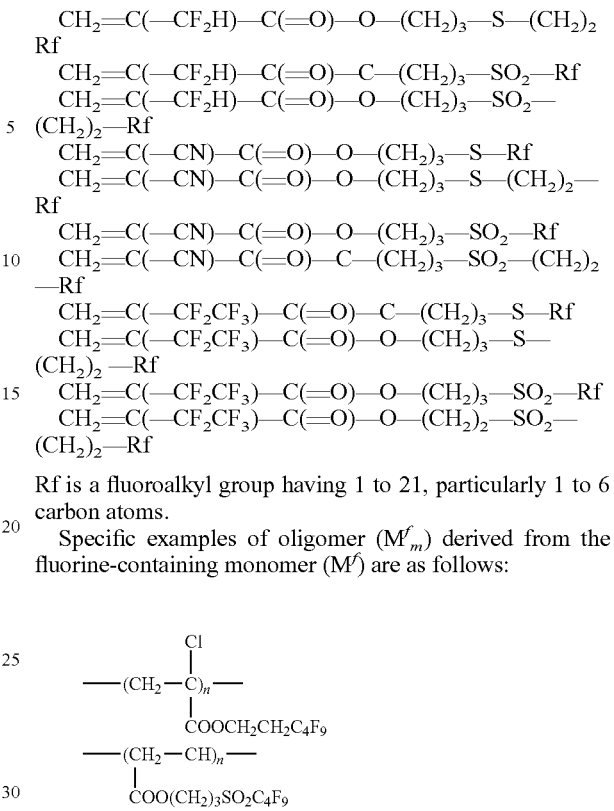

The amount of the fluorine-containing monomer ($M^f$) is preferably from 1 to 98% by weight, for example, 30 to 95% by weight, particularly 60 to 84% by weight, based on the fluorine-containing macromonomer (a).

A fluorine-free monomer ($M^r$) may be present in the formula (I). Alternatively, the fluorine-free monomer ($M^r$) may be absent in the formula (I).

The amount of the fluorine-free monomer ($M^r$) is preferably from 0 to 39% by weight, particularly 1 to 15% by weight, based on the fluorine-containing macromonomer (a).

The fluorine-free monomer ($M^r$) is a polymerizable monomer having an unsaturated double bond. The fluorine-free monomer may be any compound provided that it is free of a functional group (for example, a hydroxyl group) which causes a problem when the reactive fluorine-containing oligomer is reacted to give a macromer. The fluorine-free monomer is selected with considering the impartation of softness to the copolymer, the impartation of hydrophilicity to the copolymer, the improvement of adherence to a substrate, the solubility in a solvent.

The fluorine-free monomer ($M^r$) may be a mixture of at least two.

Specific examples of the fluorine-free monomer ($M^r$) include, for example, the followings, but are not limited to: N,N-dimethylaminoethyl (meth)acrylate, N,N-diethylaminoethyl (meth)acrylate, butadiene, vinyl acetate, styrene, chloroprene, a vinyl halide such as vinyl chloride, ethylene, a vinylidene halide such as vinylidene chloride, a vinyl alkyl ether, styrene, alkyl (meth)acrylate such as 2-ethylhexyl (meth)acrylate, cyclohexyl (meth)acrylate and stearyl (meth)acrylate, vinylpyrrolidone, and an isocyanate group-containing (meth)acrylate in which an isocyanate group is blocked with a blocking agent such as methyl ethyl ketoxime.

Specific examples of the oligomer ($M^r_n$) derived from the fluorine-free monomer ($M^r$) include the followings:

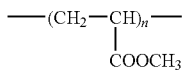

wherein n is 2 to 10,

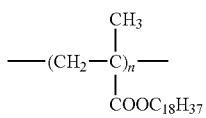

wherein n is 2 to 10, and

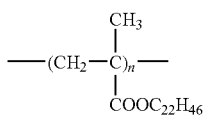

wherein n is 2 to 5.

The fluorochemical oligomer ($M^f_m M^r_n$) may be such that the monomer repeating units are not positioned as shown. The fluorochemical oligomer ($M^f_m M^r_n$) comprising at least two types of monomers may be a block polymer or a random polymer.

The fluorine-containing macromonomer (a) can be prepared as follows:

(1) A fluorine-containing monomer ($M^f$), optionally a fluorine-free monomer ($M^r$) and the active hydrogen-containing mercaptan are reacted to give a reactive fluorine-containing oligomer.

(2) The reactive fluorine-containing oligomer is reacted with a (meth)acryloyl monomer having a functional group capable of reacting with active hydrogen.

The active hydrogen-containing mercaptan includes an alkylene chain transfer agent or an aryl chain transfer agent having an active hydrogen group. Examples of the reactive group containing active hydrogen in the active hydrogen-containing mercaptan include a hydroxyl group, a carboxylic acid group and an amino group. The amount of the active hydrogen-containing mercaptan may be 0.01 to 0.5 mol, for example, 0.05 to 0.5 mol, particularly 0.1 to 0.3 mol, based on 1 mol of total of the fluorine-containing monomer ($M^f$) and the fluorine-free monomer ($M^r$).

Specific examples of the active hydrogen-containing mercaptan include the followings, to which it is not limited:

$HS(CH_2)_n OH$ n=2, 4, 6, 11

$HSCH_2COOH$ $HSCH_2CH_2COOH$ $HSCH_2CH(CH_3)COOH$ $HS-C_6H_4-COOH$ $HS-C_6H_4-OH$ $HS-C_6H_4-NH_2$

A polymerization method of producing the reactive fluorine-containing oligomer which is precursor is not limited. Various polymerization methods such as a bulk polymerization, a solution polymerization, an emulsion polymerization and a radiation polymerization can be selected. A solution polymerization using an organic solvent is preferable in view of a subsequent reaction of producing the macromonomer.

Suitable organic solvents include a polar solvent, a hydrocarbon solvent and a fluorine-containing solvent free of a functional group (for example, a hydroxyl group) which causes a problem during the preparation of a macromonomer. Examples thereof include pentane, hexane, heptane, octane, cyclohexane, benzene, toluene, xylene, petroleum ether, tetrahydrofuran, 1,4-dioxane, methyl ethyl ketone, ethyl acetate, butyl acetate, 1,1,2,2-tetrachloroethane, 1,1,1-trichloroethylene, perchloroethylene, tetrachlorodifluoroethane and trichlorotrifluoroethane. The organic solvent is used in an amount within a range from 50 to 1,000 parts by weight, based on 100 parts by weight of the total of the monomer.

The polymerization initiator includes, for example, azobisisobutyronitrile, benzoyl peroxide, di-tertiary-butyl peroxide, lauryl peroxide, cumenhydro peroxide, t-butylperoxy pivalate and diisopropylperoxy dicarbonate. The polymerization initiator is used in an amount within a range from 0.01 to 5 parts by weight, based on 100 parts by weight of the monomer.

In the solution polymerization, it is possible to employ a method of dissolving the monomer and the active hydrogen-containing mercaptan in an organic solvent in the presence of a polymerization initiator, replacing the atmosphere by nitrogen, and heating and stirring the solution at a temperature within a range from 50 to 120° C. for 1 to 10 hours, to give the reactive fluorine-containing oligomer which is a precursor.

The thus obtained reactive fluorine-containing oligomer is reacted with the (meth)acryloyl monomer having a functional group reactive with active hydrogen to give the fluorine-containing macromonomer (a) of the formula (I). Examples of the (meth)acryloyl monomer having a functional group include a glycidyl (meth)acrylate, a (meth)acryloyl chloride, and an isocyanate group-containing (meth)acrylate.

The glycidyl (meth)acrylate includes compounds of the following formulas:

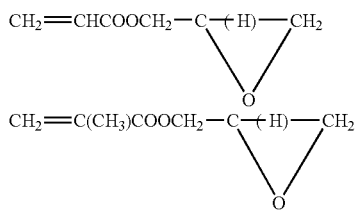

The (meth)acryloyl chloride includes compounds of the following formulas:

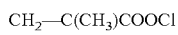

The isocyanate group-containing (meth)acrylate includes the following compounds:

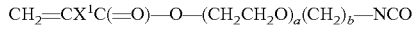

wherein $X^1$ is a hydrogen atom or a methyl group, a is 0 to 20, and b is 1 to 20. Examples of the isocyanate group-containing (meth)acrylate include 2-isocyanatoethyl (meth)acrylate.

The (meth)acryloyl monomer having a functional group is reacted with the reactive fluorine-containing oligomer in an organic solvent, if necessary with using a catalyst, for example, at a reaction temperature of room temperature to 120° C. for a reaction time of 1 to 10 hours to give a fluorine-containing macromonomer (a).

The catalyst to be used include conventional catalysts, for example, dibutyl tin dilaurate and a tertiary amine for urethanization reaction; a Lewis acid such as $SnCl_4$ for the reaction between the glycidyl group and the hydroxyl group; a tertiary amine such as triethylamine for the reaction between the glycidyl group and the carboxylic acid group.

With respect to specific examples of fluorine-containing macromonomer (a), specific examples of X, Y, Z in the general formula (I) are as follows:

leneglycol (meth)acrylate (b) is preferably a compound in which R in general formula (II) is an ethylene group.

Specific examples of the polyalkyleneglycol (meth)acrylate (b) include, but are not limited to, the followings:

$CH_2{=}CHCOO{-}(CH_2CH_2O)_9{-}H$ $CH_2{=}C(CH_3)COO{-}(CH_2CH_2O)_9{-}H$ $CH_2{=}C(CH_3)COO{-}(CH_2CH_2O)_5{-}CH_3$ $CH_2{=}C(CH_3)COO{-}(CH_2CH_2O)_9{-}CH_3$

| Example | X | Y | Z | $M^f_m$ | $M^r_n$ |
|---|---|---|---|---|---|
| 1 | —H | —$(CH_2)_b$NHCO— | —O$(CH)_d$—S— | $M1^f_m$ | — |
| 2 | —H | — | —$(CH)_d$—S— | $M1^f_m$ | — |
| 3 | —$CH_3$ | —$CH_2CH(OH)CH_2$— | —O$(CH)_d$—S— | $M1^f_m$ | — |
| 4 | —$CH_3$ | —$CH_2CH(OH)CH_2$— | —O$(CH)_d$—S— | $M1^f_m$ | $M1^r_n$ |
| 5 | —H | —$(CH_2)_b$NHCO— | —O$(CH)_d$—S— | $M2^f_m$ | — |
| 6 | —H | —$(CH_2)_b$NHCO— | —O$(CH)_d$—S— | $M2^f_m$ | $M1^r_n$ |
| 7 | —H | —$(CH_2)_b$NHCO— | —O$(CH)_d$—S— | $M3^f_m$ | — |
| 8 | —H | — | —$(CH)_d$—S— | $M3^f_m$ | — |
| 9 | —$CH_3$ | —$CH_2CH(OH)CH_2$— | —O$(CH)_d$—S— | $M3^f_m$ | $M2^r_n$ |
| 10 | —$CH_3$ | — | —O$(CH)_d$—S— | $M1^f_m$ | $M2^r_n$ |
| 11 | —$CH_3$ | —$CH_2CH(OH)CH_2$— | —COO—$(CH)_d$—S— | $M2^f_m$ | $M2^r_n$ |
| 12 | —H | —$(CH_2)_b$NHCO— | —NH—$(CH)_d$—S— | $M3^f_m$ | $M1^r_n$ | b is the number of 1 to 5.
d is the number of 1 to 5.
$M1^f_m$: $M1^f$: $CH_2{=}C(-H)-C({=}O)-O-(CH_2)_3-SO_2-Rf$ m: 2 to 20, Rf: —$C_4F_9$, —$C_6F_{13}$, —$C_8F_{17}$
$M2^f_m$: $M2^f$: $CH_2{=}C(-H)-C({=}O)-O-CH_2CH_2-Rf$ m: 2 to 30, Rf: —$C_4F_9$, —$C_6F_{13}$, —$C_8F_{17}$
$M3^f_m$: $M3^f$: $CH_2{=}C(-CH_3)-C({=}O)-OCH_2CH_2N(C_2H_5)SO_2-Rf$ m: 2 to 30, Rf: —$C_4F_9$, —$C_6F_{13}$, —$C_8F_{17}$
$M1^r_n$: $M1^r$: $CH_2{=}C(-H)-C({=}O)-O-C_2H_5$, n: 1 to 4
$M2^r_n$: $M2^r$: $CH_2{=}C(-H)-C({=}O)-O-C_{18}H_{37}$, n: 1 to 3

The polyalkyleneglycol (meth)acrylate (b) may be, polyalkyleneglycol mono(meth)acrylate and/or polyalkyleneglycol di(meth)acrylate. The molecular weight of the polyalkyleneglycol (meth)acrylate (b) may be at least 500, for example, at least 1000, particularly at least 1500. The molecular weight of the polyalkyleneglycol (meth)acrylate may be, for example, at most 6000.

The polyalkyleneglycol mono(meth)acrylate is preferably of the general formula (II):

$$CH_2{=}CX^1C({=}O)-O-(RO)_n-X^2 \quad (II)$$

wherein $X^1$ is a hydrogen atom or a methyl group, $X^2$ is a hydrogen atom or an unsaturated or saturated hydrocarbon group having 1 to 22 carbon atoms, R is an alkylene group having 2 to 6 carbon atoms, and n is an integer of 2 to 90. n may be particularly from 2 to 30, for example, 2 to 20.

In the general formula (II) for the monomer (b), R is particularly preferably an ethylene group.

In the general formula (II) for the monomer (b), R may be a combination of two or more types of alkylene groups. In this case, at least one R is preferably an ethylene group. Examples of the combination for R include a combination of an ethylene group/a propylene group and a combination of an ethylene group/a butylene group.

The polyalkyleneglycol (meth)acrylate (b) may be a mixture of two or more types. In this case, at least one polyalky- $CH_2{=}C(CH_3)COO{-}(CH_2CH_2O)_{23}{-}CH_3$ $CH_2{=}C(CH_3)COO{-}(CH_2CH_2O)_{90}{-}CH_3$ $CH_2{=}C(CH_3)COO{-}(CH_2CH(CH_3)O)_9{-}H$ $CH_2{=}CHCO{-}(CH_2CH(CH_3)O)_9{-}H$ $CH_2{=}C(CH_3)COO{-}(CH_2CH(CH_3)O)_9{-}CH_3$ $CH_2{=}C(CH_3)COO{-}(CH_2CH(CH_3)O)_{12}{-}CH_3$ $CH_2{=}C(CH_3)COO{-}(CH_2CH_2O)_5{-}(CH_2CH(CH_3)O)_2{-}H$ $CH_2{=}C(CH_3)COO{-}(CH_2CH_2O)_5{-}(CH_2CH(CH_3)O)_3{-}CH_3$ $CH_2{=}C(CH_3)COO{-}(CH_2CH_2O)_8{-}(CH_2CH(CH_3)O)_6{-}CH_2CH(C_2H_5)C_4H_9$ $CH_2{=}C(CH_3)COO{-}(CH_2CH_2O)_{23}{-}OOC(CH_3)C{=}CH_2$ $CH_2{=}C(CH_3)COO{-}(CH_2CH_2O)_{20}{-}(CH_2CH(CH_3)O)_5{-}CH_2{-}CH{=}CH_2$ In the fluorine-containing copolymer of the present invention, the amount of the monomer (a) (that is, the repeating unit (A)) may be from 20 to 90% by weight, preferably from 30 to 85% by weight, for example, from 35 to 80% by weight, and particularly from 50 to 75% by weight, based on the total of the component (a) and the component (b). When the amount is from 20% to 90% by weight, high soil releasability can be attained and also intrusion of oil stains can be prevented.

The amount of the component (b) (that is, the repeating unit (B)) may be from 10 to 80% by weight, preferably from 15 to 70% by weight, for example, from 20 to 65% by weight, and particularly from 25 to 50% by weight, based on the total of the component (a) and the component (b). When the amount is from 10% to 80% by weight, high soil releasability can be attained and also intrusion of oil stains can be prevented.

For the purpose of an improvement in durable soil releasability, solubility in an organic solvent and adhesion to an article to be treated to which flexibility is imparted, another polymerizable monomer [that is, a monomer (c)], particularly a non-fluorine monomer may be introduced into the fluorine-containing copolymer of the present invention.

Specific examples of the component (c) include, but are not limited to, diacetoneacrylamide, (meth)acrylamide, N-methylolacrylamide, hydroxyethyl (meth)acrylate, 3-chloro-2-hydroxypropyl (meth)acrylate, N,N-dimethylaminoethyl (meth)acrylate, N,N-diethylaminoethyl (meth)acrylate, butadiene, chloroprene, glycidyl (meth)acrylate, a maleic acid derivative, vinyl chloride, ethylene, a vinylidene halide, a vinyl alkyl ether, glycerol (meth)acrylate, styrene, acetoacetoxyethyl (meth)acrylate, an alkyl (meth)acrylate, vinylpyrrolidone, a silicon-containing monomer such as (meth)acryloxytrialkylsilane and (meth)acryloxy-trialkoxysilane, and an isocyanate group-containing (meth)acrylate such as 2-isocyanate ethyl methacrylate or (meth)acrylate in which an isocyanate group is blocked with a blocking agent such as methyl ethyl ketoxime.

The copolymerization proportion of the monomer (c) may be from 0 to 40% by weight, and preferably from 0 to 30% by weight, for example, 0.1 to 20% by weight, based on the fluorine-containing copolymer. The monomer (c) may be a mixture of two or more types.

The weight-average molecular weight of the fluorine-containing copolymer of the present invention may be from 1,000 to 1,000,000, and preferably from 5,000 to 500,000. When the weight-average molecular weight is from 1,000 to 1,000,000, high soil releasability is obtained while maintaining durability and a polymer liquid has low viscosity so that it is easy to handle. The molecular weight is a polystyrene equivalent value determined using gel permeation chromatography.

A polymerization method of producing the copolymer of the present invention is not limited. Various polymerization methods such as a bulk polymerization, a solution polymerization, an emulsion polymerization and a radiation polymerization can be selected. For example, a solution polymerization using an organic solvent and an emulsion polymerization using water or both an organic solvent and water are generally selected. A treatment liquid is produced by diluting a reaction mixture with water or adding an emulsifying agent to make the emulsification after the polymerization.

Examples of the organic solvent include ketones such as acetone and methyl ethyl ketone; esters such as ethyl acetate and methyl acetate; glycols such as propylene glycol, dipropylene glycol monomethyl ether, dipropylene glycol, tripropylene glycol and low molecular weight polyethylene glycol; and alcohols such as ethyl alcohol and isopropanol.

As the emulsifying agent for the emulsion polymerization and for emulsification in water by adding the emulsifying agent, various emulsifying agents such as an anionic emulsifying agent, a cationic emulsifying agent and a nonionic emulsifying agent can be used.

As the polymerization initiator, for example, peroxide, an azo compound or a persulfuric acid-based compound can be used. The polymerization initiator is generally water-soluble and/or oil-soluble.

Specific examples of the oil-soluble polymerization initiator are preferably 2,2'-azobis(2-methylpropionitrile), 2,2'-azobis(2-methylbutyronitrile), 2,2'-azobis(2,4-dimethylvaleronitrile), 2,2'-azobis(2,4-dimethyl-4-methoxyvaleronitrile), 1,1'-azobis(cyclohexane-1-carbonitrile), dimethyl 2,2'-azobis(2-methylpropionate), 2,2'-azobis(2-isobutyronitrile), benzoyl peroxide, di-tertiary-butyl peroxide, lauryl peroxide, cumenhydro peroxide, t-butylperoxy pivalate, diisopropylperoxy dicarbonate, and t-butyl perpivalate.

Specific examples of the water-soluble polymerization initiator are preferably 2,2'-azobisisobutylamidine dihydrochloride, 2,2'-azobis(2-methylpropionamidine) hydrochloride, 2,2'-azobis[2-(2-imidazolin-2-yl)propane]hydrochloride, 2,2'-azobis[2-(2-imidazolin-2-yl)propane]sulfate hydrate, 2,2'-azobis[2-(5-methyl-2-imidazolin-2-yl)propane]hydrochloride, potassium persulfate, barium persulfate, ammonium persulfate, and hydrogen peroxide.

The polymerization initiator is used in an amount within a range from 0.01 to 5 parts by weight based on 100 parts by weight of the monomer.

For the purpose of adjusting the molecular weight, a known mercapto group-containing compound may be used, and specific examples thereof include 2-mercaptoethanol, thiopropionic acid, and alkyl mercaptan. The mercapto group-containing compound is used in an amount of 5 parts by weight or less, within a range from 0.01 to 3 parts by weight, based on 100 parts by weight of the monomer.

Specifically, a copolymer can be produced in the following manner.

In the solution polymerization, it is possible to employ a method of dissolving a monomer in an organic solvent in the presence of a polymerization initiator, replacing the atmosphere by nitrogen and stirring the solution with heating at a temperature within a range from 50 to 120° C. for 1 to 10 hours. The polymerization initiator generally may be an oil-soluble polymerization initiator. The organic solvent is inert to the monomer and dissolves it, and examples of the monomer include pentane, hexane, heptane, octane, cyclohexane, benzene, toluene, xylene, petroleum ether, tetrahydrofuran, 1,4-dioxane, methyl ethyl ketone, methyl isobutyl ketone, ethyl acetate, butyl acetate, 1,1,2,2-tetrachloroethane, 1,1,1-trichloroethane, trichloroethylene, perchloroethylene, tetrachlorodifluoroethane, and trichlorotrifluoroethane. The organic solvent is used in an amount within a range from 50 to 1,000 parts by weight based on 100 parts by weight of the total of the monomer.

In an emulsion polymerization, there can be used a method of emulsifying monomers in water in the presence of a polymerization initiator and an emulsifying agent, replacing the atmosphere by nitrogen, and polymerizing with stirring, for example, at the temperature within the range front 50° C. to 80° C. for 1 hour to 10 hours.

In order to obtain a polymer dispersion in water, which is superior in storage stability, it is desirable that the monomers are dispersed in water by using an emulsifying device capable of applying a strong shearing energy (e.g., a high-pressure homogenizer and an ultrasonic homogenizer) and then polymerized with using the water-soluble polymerization initiator. As the emulsifying agent, various emulsifying agents such as an anionic emulsifying agent, a cationic emulsifying agent and a nonionic emulsifying agent can be used in the amount within the range from 0.5 to 10 parts by weight based on 100 parts by weight of the monomers. When the monomers are not completely compatibilized, a compatibilizing agent (e.g., a water-soluble organic solvent and a low-molecular weight monomer) capable of sufficiently compatibilizing them is preferably added to these monomers. By the addition of the compatibilizing agent, the emulsifiability and copolymerizability can be improved.

Examples of the water-soluble organic solvent include acetone, methyl ethyl ketone, ethyl acetate, propylene glycol, dipropylene glycol monomethyl ether, dipropylene glycol, tripropylene glycol and ethanol. The water-soluble organic solvent may be used in the amount within the range from 1 to 80 parts by weight, e.g., from 5 to 50 parts by weight, based on 100 parts by weight of water.

The copolymer thus obtained can be formed into any form such as an emulsion, an organic solvent solution or an aerosol after optionally diluting with or dispersing in water or an organic solvent, and thus a soil release agent can be obtained. The copolymer functions as an active ingredient of the soil release agent. The soil release agent comprises a fluorine-containing copolymer and a medium (particularly, a liquid medium) (for example, an organic solvent and/or water). In the soil release agent, the concentration of the fluorine-containing copolymer is, for example, from 0.01 to 50% by weight.

The soil release agent of the present invention preferably comprises a fluorine-containing copolymer and an aqueous medium. As used herein, the term "aqueous medium" means a medium comprising only water, and a medium containing, in addition to water, an organic solvent (the amount of the organic solvent is 80 parts by weight or less, for example, 5 to 50 parts by weight, based on 100 parts by weight of water).

The copolymer of the present invention can be applied to an article to be treated, as a soil release agent, according to the type and the preparation form of an article to be treated (an emulsion, an organic solvent solution, or an aerosol) using an optional method. In the case of an aqueous emulsion or an organic solvent solution, a method of coating on the surface of an article to be treated using a known method, for example, a coating method such as a dip coating or spray coating method, followed by drying can be employed. In this case, a heat treatment such as curing may be performed, if necessary.

If necessary, another blender can be used in combination. Examples of the blender include water- and oil-repellents, anti-wrinkle agents, anti-shrinkage agents, flame retardants, crosslinking agents, antistatic agents, softening agents, water-soluble polymers such as polyethylene glycol and polyvinyl alcohol, wax emulsions, antibacterial agents, pigments, and coating materials. These blenders may be added to a treating bath upon treatment of an article to be treated. If possible, the blenders may be preliminarily mixed with the copolymer of the present invention.

The substrate to be treated with the surface treatment agent (for example, a water- and oil-repellent agent) of the present invention include a textile, masonry, a filter (for example, an electrostatic filter), a dust protective mask, a part of fuel cell (for example, a gaseous diffusion electrode and a gaseous diffusion support), glass, paper, wood, leather, fur, asbestos, brick, cement, metal and oxide, ceramics, plastics, a coated surface and a plaster. The textile may be particularly a carpet. The textile has various examples. Examples of the textile include animal- or vegetable-origin natural fibers such as cotton, hemp, wool and silk; synthetic fibers such as polyamide, polyester, polyvinyl alcohol, polyacrylonitrile, polyvinyl chloride and polypropylene; semi-synthetic fibers such as rayon and acetate; inorganic fibers such as glass fiber, carbon fiber and asbestos fiber; and a mixture of these fibers. The textile may be in any form such as a fiber, a yarn, a fabric and the like.

In the present invention, a substrate is treated with a soil release agent. The "treatment" means that a treatment agent is applied to a substrate by immersions spraying, coating or the like. The treatment gives the result that a fluorine-containing polymer which is an active component of the treatment agent is penetrated into the internal parts of the substrate and/or adhered to surfaces of the substrate.

EXAMPLES

The present invention is now described in detail by way of Synthetic Examples, Examples, Comparative Examples and Test Examples. However, the present invention is not limited to these.

In the following Examples, Comparative Examples and Test Examples, parts and percentages are by weight unless otherwise specified.

Tests were Performed in the Following Manner.

(1) Soil Release (SR Property) Test

A soil release test was performed in accordance with AATCC Soil Release Management Performance Test Method of USA. As soils for the test, an artificial oil, which is not easily removed by washing, was used in place of cone oil. The artificial oil was prepared by adding 100 ml of Daphne Mechanic Oil (manufactured by Idemitsu Kosan Co., Ltd.) to 1 g of a diamond paste consisting of 16.7% of carbon black, 20.8% of beef tallow superhardened oil and 62.5% of liquid paraffin.

A test cloth having a size of 20 cm×20 cm was spread out on a horizontally spread absorbent blotting paper, and five drops of the artificial oil (about 0.2 cc) as the soil were dropped. A glassine paper was laid thereon and a weight of 2,268 g was placed, followed by standing for 60 seconds. After 60 seconds, the weight and the glassine paper were removed, followed by standing at room temperature for 15 minutes. After the lapse of 15 minutes, the test cloth and a ballast cloth (total weight: 1.8 kg) were washed under the conditions of a bath volume of 64 liters and a bath temperature of 38° C. for 12 minutes using 100 g of a detergent (an AATCC standard WOB detergent) and an AATCC standard washing machine (manufactured by Kenmore, USA) rinsed and then dried using an AATCC standard tumbler drying machine (manufactured by Kenmore, USA). The state of the remaining soil on the dried test cloth was compared with that of a standard photographic plate for criterion and expressed by the corresponding criterion class (see Table 1). As the standard photographic plate for criterion, a photographic plate of AATCC-TM130-2000 (American Association of Textile Chemists and Colorists Test Method 130-2000) was used.

TABLE 1

Criterion class of soil releasability

| Class | Criterion |
|---|---|
| 1.0 | Remarkable soil remained |
| 2.0 | Considerable soil remained |
| 3.0 | Slight soil remained |
| 4.0 | Little soil remained |
| 5.0 | No soil remained |

(2) Oil Repellency Test

An oil repellency test was performed in accordance with AATCC-TM118-2000 using a textile. A test cloth was spread out and several drops of a test liquid shown in Table 2 were dropped. It was evaluated by the state of the test liquid which passes the test cloth after 30 seconds. In the case of low oil repellency, an oil soil intrudes into an article to be treated, thus making it difficult to remove the oil soil. Therefore, oil repellency is an important evaluation indicator, similar to a test of soil releasability (SR properties).

TABLE 2

| Criterion class of oil repellency | | |
|---|---|---|
| Oil repellency | Test solution | Surface tension (dyne/cm, 25° C.) |
| 8 | n-heptane | 20.0 |
| 7 | n-octane | 21.8 |
| 6 | n-decane | 23.5 |
| 5 | n-dodecane | 25.0 |
| 4 | n-tetradecane | 26.7 |
| 3 | n-hexadecane | 27.3 |
| 2 | Mixed liquid of hexadecane/Nujor (35/65) | 29.6 |
| 1 | Nujor | 31.2 |
| 0 | Inferior to 1 | — |

Synthesis Example 1

9FSO2PA Monomer

Synthesis of 3-(perfluorobutylsulfonyl)propyl acrylate

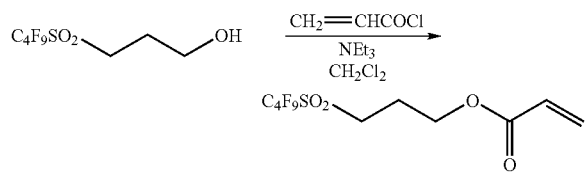

A solution of 3-(perfluorobutylsulfonyl)propanol (54.4 g, 159 mmol), triethylamine (33 ml, 238 mmol), 4-t-butylcatechol (0.14 g) and dichloromethane (520 ml) was cooled to 0° C. in a state of being equipped with a calcium chloride, and then acryloyl chloride (15.5 ml, 191 mmol) was slowly added dropwise over 40 minutes. After stirring at room temperature for one hour and washing the mixture with 15% citric acid (600 ml) water and saturated saline, the mixture was dried over anhydrous magnesium sulfate, filtered and then concentrated under reduced pressure to obtain a crude acrylate ester. The residue was purified by silica gel column chromatography (n-hexane:ethyl acetate=6:1) and the transparent liquid was vacuum-dried after concentration to obtain 60.0 g of 3-(perfluorobutylsulfonyl)propyl acrylate. Yield was 95.3%.

$^1$H NMR (CDCl$_3$; internal standard TMS δppm): 6.45 (dd, 1H, $J_{AB}$=1.1 Hz, $J_{AX}$=17.3 Hz, CH$_A$H$_B$=C), 6.12 (dd, 1H, $J_{AX}$=17.3 Hz, $J_{BX}$=10.5 Hz, C=CH$_X$), 5.95 (dd, 1H, $J_{BX}$=10.5 Hz, $J_{AB}$=1.1 Hz, CH$_A$H$_B$=C), 4.34 (t, 2H, $J_{HH}$=6.1 Hz, OCH$_2$), 3.41 (t, 2H, $J_{AB}$=7.8 Hz, CH$_2$SO$_2$), 2.36 (tt, 2H, $J_{HH}$=7.8 Hz, $J_{HH}$=6.0 Hz, CH$_2$CH$_2$CH$_2$). $^{19}$F NMR (CDCl$_3$; internal standard CFCl$_3$ δ ppm): —81.2 (m, 3F, CF$_3$), —113.8 (m, 2F, CF$_2$SO$_2$), —121.8 (m, 2F, CF$_2$), -126.3 (m, 2F, CF$_2$).

Synthetic Example 2

Synthesis of 9FSO2PA-M1 (Macromer))

9FSO2PA monomer (50 g) prepared in Synthetic Example 1, 2-mercaptoethanol (1.97 g) and ethyl acetate (78 g) were charged into a four-necked flask equipped with a nitrogen inlet tube and then heated to 80° C. Nitrogen bubbling was initiated and, after 30 minutes, azobisisobutyronitrile (0.33 g) was charged to conduct the polymerization for 8 hours. After the disappearance of peaks of the monomers and 2-mercaptoethanol was confirmed, the reaction system was cooled to 60° C., t-butylhydroxy toluene (0.0022 g) and dibutyltin dilaurate (0.01 g) were charged. 2-methacryloyoxyethyl isocyanate (1.457 g) was gradually added to conduct the reaction for 3 hours. After the disappearance of peaks of isocyanate group was confirmed by infra red spectrum, ethyl acetate was distilled off to give a macromer (9FSO2PA-M1). The degree of polymerization of the macromer was 5.5 on average.

Synthetic Example 3

Synthesis of 9FSO2PA-M2 (macromer))

9FSO2PA monomer (50 g) prepared in Synthetic Example 1, 2-mercaptoethanol (1.97 g) and ethyl acetate (78 g) were charged into a four-necked flask equipped with a nitrogen inlet tube and then heated to 80° C. Nitrogen bubbling was initiated and, after 30 minutes, azobisisobutyronitrile (0.33 g) was charged to conduct the polymerization for 8 hours. After the disappearance of peaks of the monomers and 2-mercaptoethanol was confirmed, the reaction system was cooled to room temperature. Triethylamine (1.533 g) and hydroquinone (0.014 g) were added to the reaction system, and methacryloyl chloride (1.32 g) was gradually added with caution to exothermic heat.

The reaction was conducted at room temperature for 3 hours and then the disappearance of peak of methacryloyl chloride was confirmed. The reaction liquid was washed with saturated aqueous saline solution, an oily layer was separated, a small amount of magnesium sulfate anhydride was added and the mixture was kept standing for one night. Ethyl acetate was distilled off under a reduced pressure to give a macromer (9FSO2PA-M2). The degree of polymerization of the macromer was 5.5 on average.

Copolymers were Prepared as Follows.

Example 1

In a 100 ml four-necked flask, 7.0 g of the macromer (9FSO2PA-M1) synthesized in Synthesis Example 2, methoxy-polyethylene glycol methacrylate (EO 23 mol) (2.0 g), 2-hydroxyethyl methacrylate (0.8 g), 2-methacryloyloxyethyl-trimethylammonium chloride (0.2 g) and dipropylene glycol monomethyl ether (29 g) were charged and nitrogen flow was performed for 60 minutes. After the inner temperature was raised to 75-80° C., azobisisobutyronitrile (0.1 g) dissolved in methyl ethyl ketone (1 g) was added and the reaction was performed for B hours. The resulting polymerization liquid was subjected to a gel permeation chromatography to measure the molecular weight. The measurement revealed that a peak derived from the monomer approximately disappeared and a peak derived from the copolymer is generated. The weight-average molecular weight of the copolymer was 11,000 (in terms of polystyrene).

Examples 2 to 6

Copolymer solutions were obtained by repeating the same procedure as in Example 1 except using the types and weight ratios of the monomers shown in Table 3. The ingredients and the weight-average molecular weights of the copolymers are shown in Table 3.

Examples 7 to 8

Copolymer solutions were obtained by repeating the same procedure as in Example 1 except replacing the 9FSO2PA-M1 macromer with the 9FSO2PA-M2 macromer and using the types and weight ratios of the monomers shown in Table 3. The ingredients and the weight-average molecular weights of the copolymers are shown in Table 3.

Examples 9 to 10

Copolymer solutions were obtained by repeating the same procedure as in Example 1 except using the types and weight ratios of the monomers shown in Table 3. The ingredients and the weight-average molecular weights of the copolymers are shown in Table 3.

Comparative Examples 1 to 4

Copolymer solutions were obtained by repeating the same procedure as in Example 1 except replacing the 9FSO2PA-M1 macromer with a 9FSO2PA monomer and using the types and weight ratios of the monomers shown in Table 3. The ingredients and the weight-average molecular weights of the copolymers are shown in Table 3.

Test Example 1

The polymer solution obtained in Example 1 was diluted with water to prepare a water dispersion having a copolymer content of 0.86% by weight. In this case, stearyltrimethylammonium chloride was added in the amount of 1.5% by weight based on the polymer for the purpose of facilitating dispersion. A cotton twill cloth was immersed in the treatment solution thus obtained, and then squeezed with a roll, thereby adjusting wet pickup to 60% by weight. The cloth was dried at 110° C. for 2 minutes and then heat-treated at 160° C. for 2 minutes, thereby completing a soil releasing treatment. Soil releasability and oil repellency of the cloth were measured. The results are shown in Table 4.

For the purpose of evaluating washing durability, a the treated cloth was washed at a bath temperature of 40° C. for 25 minutes using a washing machine, and tumbler-dried (This test corresponds to HL5. HL10 is 2 cycles of HL5. HL20 is 4 cycles of HL5). Soil releasability and oil repellency of the treated cloth were measured in the same manner as described above. The results are shown in Table 5.

Test Examples 2 to 10 and Comparative Test Examples 1 to 4

Treatment solutions were prepared by the same procedure as in Test Example 1, except that the polymer solution was replaced by each polymer solution obtained in Examples 2 to 10 and Comparative Examples 1 to 4, and the cloths were treated and then soil releasability and oil repellency were measured.

The results are shown in Table 5.

The data of oil repellency for Examples 1 to 6 and Comparative Examples 1 to 4 of Table 5 are depicted in FIG. 1 having plotted data on a horizontal axis of fluorine content (% by weight) in a polymer and a vertical axis of oil repellency. The polymer comprising the 9FSO2PA-M1 macromer as a fluorine component has higher properties than the polymer comprising the 9FSO2PA monomer, even if the polymer has low fluorine content in the polymer.

Figure 2:
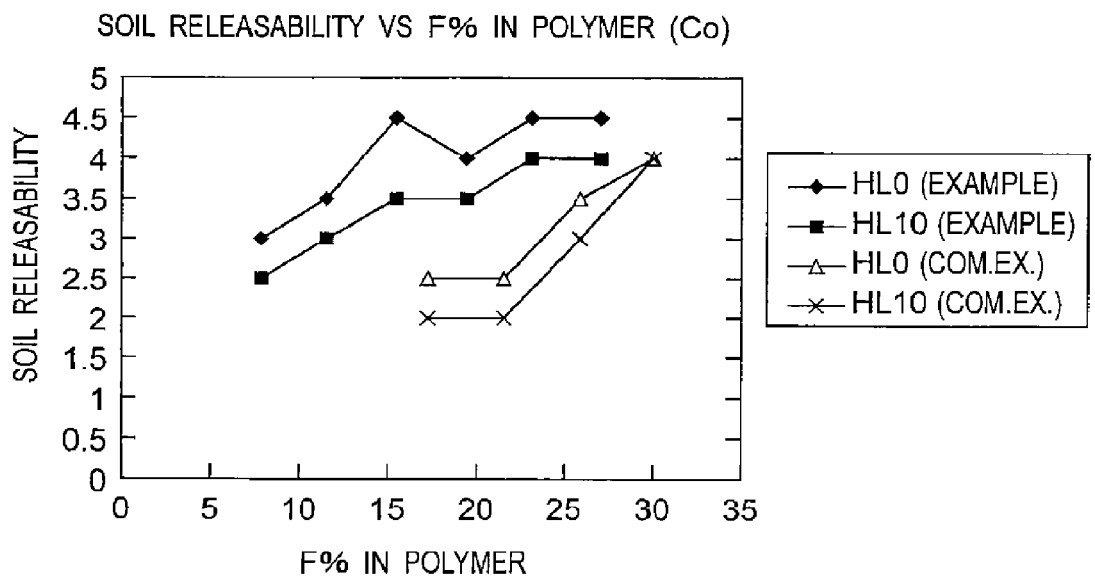
FIG. 2 is a graph showing the relationship between a fluorine content in a polymer (% by weight) and soil releasability.

The data of soil releasability for Examples 1 to 6 and Comparative Examples 1 to 4 of Table 5 are depicted in FIG. 2 having plotted data on a horizontal axis of fluorine content (% by weight) in a polymer and a vertical axis of soil releasability (SR property). The polymer comprising the 9FSO2PA-M1 macromer as a fluorine component has higher properties than the polymer comprising the 9FSO2PA monomer, even if the polymer has low fluorine content in the polymer.

TABLE 3

| | Monomer ingredients | Monomer weight ratio (%) | Weight-average molecular weight of polymer |
|---|---|---|---|
| Example 1 | 9FSO2PA-M1/M-230G/HEMA/DQ-100 | 70/20/8/2 | 10000 |
| Example 2 | 9FSO2PA-M1/M-230G/HEMA/DQ-100 | 60/30/8/2 | 11000 |
| Example 3 | 9FSO2PA-M1/M-230G/HEMA/DQ-100 | 50/40/8/2 | 13000 |
| Example 4 | 9FSO2PA-M1/M-230G/HEMA/DQ-100 | 40/50/8/2 | 13000 |
| Example 5 | 9FSO2PA-M1/M-230G/HEMA/DQ-100 | 30/60/8/2 | 14000 |
| Example 6 | 9FSO2PA-M1/M-230G/HEMA/DQ-100 | 20/70/8/2 | 15000 |
| Example 7 | 9FSO2PA-M2/M-230G/HEMA/DQ-100 | 70/20/8/2 | 9000 |
| Example 8 | 9FSO2PA-M2/M-230G/HEMA/DQ-100 | 30/60/8/2 | 16000 |
| Example 9 | 9FSO2PA-M1/AE-400/HEA/DQ-100/DMAEM | 50/40/8/1/1 | 11000 |
| Example 10 | 9FSO2PA-M1/AE-400/PP-800/HEA/DQ-100 | 50/35/5/8/2 | 11000 |
| Com. Ex. 1 | 9FSO2PA/M-230G/HEMA/DQ-100 | 70/20/8/2 | 18000 |
| Com. Ex. 2 | 9FSO2PA/M-230G/HEMA/DQ-100 | 60/30/8/2 | 17000 |
| Com. Ex. 3 | 9FSO2PA/M-230G/HEMA/DQ-100 | 50/40/8/2 | 11000 |
| Com. Ex. 4 | 9FSO2PA/M-230G/HEMA/DQ-100 | 40/50/8/2 | 12000 |

TABLE 4

(Description of abbreviation in Table 3)

| Abbreviation | Trade name | Chemical name | Manufacturer |
|---|---|---|---|
| 9FSO2PA-M1 | | Poly{2-(perfluorobutylsulphonyl)propyl acrylate} macromer (Synthetic Example 2) | |
| 9FSO2PA-M2 | | Poly{2-(perfluorobutylsulphonyl)propyl acrylate} macromer (Synthetic Example 3) | |
| 9FSO2PA | | 2-(Perfluorobutylsulphonyl)propyl acrylate | |
| M-230G | NK ESTER M-230G | Methoxypolyethylene glycol methacrylate (EO 23 mol) | Shin-nakamura Chemical Co., Ltd. |
| AE-400 | BLENMER AE-400 | Polyethylene glycol monoacrylate (EO 10 mol) | NOF Corporation |
| PP-800 | BLENMER PP-800 | Polypropylene glycol monomethacrylate (PO 13 mol) | NOF Corporation |
| HEMA | | 2-Hydroxyethyl methacrylate | |
| HEA | | 2-Hydroxyethyl acrylate | |
| DQ-100 | LIGHT-ESTER DQ-100 | 2-Methacryloyloxyethyltrimethylammonium chloride | Kyoeisha Chemical Co., Ltd. |
| DMAEM | LIGHT-ESTER DM | Dimethylaminoethyl methacrylate | Kyoeisha Chemical Co., Ltd. |

TABLE 5

| | Oil repellency | | | Soil releasability Artificial oil | | |
|---|---|---|---|---|---|---|
| | Initial | HL10 | HL20 | Initial | HL10 | HL20 |
| Example 1 | 6 | 6 | 6 | 4-5 | 4 | 4 |
| Example 2 | 6 | 5 | 5 | 4-5 | 4 | 4-5 |
| Example 3 | 5 | 5 | 4 | 4 | 3-4 | 3-4 |
| Example 4 | 5 | 4 | 4 | 4-5 | 3-4 | 3-4 |
| Example 5 | 5 | 0 | 0 | 3-4 | 3 | 3 |
| Example 6 | 5 | 0 | 0 | 3 | 2-3 | 2 |
| Example 7 | 6 | 5 | 5 | 4 | 4 | 3-4 |
| Example 8 | 5 | 0 | 0 | 3 | 3 | 2-3 |
| Example 9 | 5 | 5 | 4 | 4 | 4 | 3-4 |
| Example 10 | 5 | 5 | 4 | 4 | 4 | 3-4 |
| Com. Ex. 1 | 5 | 5 | 5 | 4 | 4 | 4 |
| Com. Ex. 2 | 4 | 0 | 0 | 3-4 | 3 | 2-3 |
| Com. Ex. 3 | 2 | 0 | 0 | 2-3 | 2 | 2 |
| Com. Ex. 4 | 1 | 0 | 0 | 2-3 | 2 | 2 |
| Untreated cloth | 0 | 0 | 0 | 1 | 1 | 1 |

Note)
The number A-B in the table means an intermediate performance between A and B.
Each of HL10 and HL20 means after washing time of 10 and after washing time of 20.

What is claimed is:

1. A fluorine-containing copolymer comprising:
(A) repeating units derived from a fluorine-containing macromonomer of the general formula:

$$CH_2=C(-X)-COO-(Y)l-Z-M^f_mM^r_n-H \quad (I)$$

wherein X is a hydrogen atom or a methyl group;
Y is —$CH_2CH(OH)CH_2$— or $R^1$—NHCO— where $R^1$ is —$(CH_2CH_2O)_a(CH_2)_b$, a is 0 to 20, and b is 1 to 20; l is 0 or 1;
Z is —$L_1$—$L_2$—S— where $L_1$ is a direct bond, —O—, COO— or NH—, $L_2$ is an alkylene group having 1 to 20 carbon atoms or an aryl group having 6 to 20 carbon atoms, and S is a sulfur atom;
$M^f_mM^r_n$ is a fluorochemical oligomer having m repeating units derived from a fluorine-containing monomer ($M^f$) and n repeating units derived from a fluorine-free monomer ($M^r$) where m is 2 to 50 and n is 0 to 20, and
(B) repeating units derived from a polyalkyleneglycol (meth)acrylate,
wherein the fluorine-free monomer ($M^r$) is a polymerizable monomer having an unsaturated double bond, and wherein the fluorine-containing monomer ($M^f$) is of the general formula:

$$CH_2=C(-X)-C(=O)-Y-[-(CH_2)_m-Z-]_p-(CH_2)_n-Rf \quad (Ia)$$

wherein X is a hydrogen atom, a methyl group, a straight-chain or branched alkyl group having 1 to 21 carbon atoms, a fluorine atom, a chlorine atom, a bromine atom, a iodine atom, a $CFX^1X^2$ group wherein $X^1$ and $X^2$ represent a hydrogen atom, a fluorine atom, a chlorine atom, a bromine atom, or an iodine atom, a cyano group, a straight-chain or branched fluoroalkyl group having 1 to 21 carbon atoms, a substituted or an unsubstituted benzyl group, or a substituted or an unsubstituted phenyl group;
Y is —O— or —NH—;
Z is —S— or —$SO_2$—;
Rf is a fluoroalkyl group having 1 to 21;
m is 1 to 10, n is 0 to 10, and p is 0 or 1.

2. The fluorine-containing copolymer according to claim 1 wherein, in the general formula (Ia) of fluorine-containing monomer ($M^f$), p and n are 0, and Y is a —$OCH_2CH_2N(R^2)SO_2$— group where $R^2$ is an alkyl group having 1 to 4 carbon atom or a —$OCH_2CH(OCOCH_3)CH_2$ group.

3. The fluorine-containing copolymer according to claim 1, wherein the polyalkyleneglycol (meth)acrylate (b) constituting the repeating unit (B) is of the general formula:

$$CH_2=CX^1C(=O)-O-(RO)_n-X^2 \quad (II)$$

wherein $X^1$ is, a hydrogen atom or a methyl group,
$X^2$ is a hydrogen atom or an unsaturated or saturated hydrocarbon group having 1 to 22 carbon atoms,
R is an alkylene group having 2 to 6 carbon atoms,
and n is an integer of 2 to 90.

4. The fluorine-containing copolymer according to claim 1, wherein, in the copolymer, the repeating unit (A) is in the amount of 20 to 90% by weight and the repeating unit (B) is in the amount of 10 to 80% by weight, based on the total of the repeating unit (A) and the repeating unit (B).

5. A fluorine-containing copolymer according to claim 1, wherein the weight-average molecular weight of the copolymer is from 1000 to 1000000.

6. A soil release agent comprising the fluorine-containing copolymer according to claim 1.

7. A textile treated with the soil release agent according to claim 6.

8. A soil release composition comprising the fluorine-containing copolymer according to claim 1, and an aqueous medium.

9. The fluorine-containing copolymer according to claim 1, wherein the fluorine-containing macromonomer ($M^f$) is at least one selected from the group consisting of:

$CH_2=C(-X)-C(=O)-O-(CH_2)m-S-(CH_2)_n-Rf$,
$CH_2=C(-X)-C(=O)-O-(CH_2)_m-SO_2-(CH_2)_n-Rf$,
$CH_2=C(-X)-C(=O)-O-(CH_2)_n-Rf$ and
$CH_2=C(-X)-C(=O)-NH-(CH_2)_n-Rf$, wherein X is a hydrogen atom, a methyl group, a fluorine atom, a chlorine atom, a bromine atom, a iodine atom, a $CFX^1X^2$ group wherein $X^1$ and $X^2$ represent a hydrogen atom, a fluorine atom, or a chlorine atom, a cyano group, a straight-chain or branched fluoroalkyl group having 1 to 20 carbon atoms, a substituted or an unsubstituted benzyl group, or a substituted or an unsubstituted phenyl group;

Rf is a fluoroalkyl group having 1 to 21 carbon atoms; and m is 1 to 10, n is 0 to 10.

10. A method for treating a substrate, which comprises treating the substrate with a soil release agent wherein said soil release agent is the fluorine-containing copolymer comprising:

(A) repeating units derived from a fluorine-containing macromonomer of the general formula:

$$CH_2=C(-X)-COO-(Y)l-Z-M^f_mM^r_n-H \quad (I)$$

wherein X is a hydrogen atom or a methyl group;
Y is $-CH_2CH(OH)CH_2-$ or $R^1-NHCO-$ where $R^1$ is $-(CH_2CH_2O)_a(CH_2)_b-$, a is 0 to 20, and b is 1 to 20; l is 0 or 1;

Z is $-L_1-L_2-S-$ where $L_1$ is a direct bond, $-O-$, $COO-$ or $NH-$, $L_2$ is an alkylene group having 1 to 20 carbon atoms or an aryl group having 6 to 20 carbon atoms, and S is a sulfur atom;

$M^f_mM^r_n$ is a fluorochemical oligomer having m repeating units derived from a fluorine-containing monomer ($M^f$) and n repeating units derived from a fluorine-free monomer ($M^r$) where m is 2 to 50 and n is 0 to 20, and (B) repeating units derived from a polyalkyleneglycol (meth)acrylate, wherein the fluorine-free monomer ($M^r$) is a polymerizable monomer having an unsaturated double bond, and wherein the fluorine-containing monomer ($M^f$) is of the general formula:

$$CH_2=C(-X)-C(=O)-Y-[-(CH_2)_m-Z-]_p-(CH_2)_n-Rf \quad (Ia)$$

wherein X is a hydrogen atom, a methyl group, a straight-chain or branched alkyl group having 1 to 21 carbon atoms, a fluorine atom, a chlorine atom, a bromine atom, a iodine atom, a $CFX^1X^2$ group wherein $X^1$ and $X^2$ represent a hydrogen atom, a fluorine atom, a chlorine atom, a bromine atom, or an iodine atom, a cyano group, a straight-chain or branched fluoroalkyl group having 1 to 21 carbon atoms, a substituted or an unsubstituted benzyl group, or a substituted or an unsubstituted phenyl group;

Y is $-O-$ or $-NH-$;
Z is $-S-$ or $-SO_2-$,
Rf is a fluoroalkyl group having 1 to 21;
m is 1 to 10, n is 0 to 10, and p is 0 or 1.

* * * * *